United States Patent [19]

Taylor et al.

[11] Patent Number: 4,615,976

[45] Date of Patent: Oct. 7, 1986

[54] SYNTHESIS AND ISOLATION OF OCTOPINE AND ITS ANALOGUES

[75] Inventors: Kenneth B. Taylor, Birmingham; Leo M. Hall, Homewood, both of Ala.

[73] Assignee: The University of Alabama in Birmingham, Ala.

[21] Appl. No.: 523,082

[22] Filed: Aug. 15, 1983

[51] Int. Cl.$^4$ .............. C07C 101/26; C07C 101/30; C07C 109/18; C07C 127/15; C07C 129/08; C12N 15/00; C12N 1/20; C12N 5/00; C07B 57/00

[52] U.S. Cl. .............................. 435/172.3; 435/240; 435/241; 435/243; 435/253; 562/402; 562/554; 562/560; 562/564; 562/565

[58] Field of Search .............. 562/402, 554, 560, 564, 562/565; 435/172.3, 240, 241, 243, 253

[56] References Cited

U.S. PATENT DOCUMENTS

| | | |
|---|---|---|
| 2,168,181 | 8/1939 | Ulrich et al. ..................... 562/565 |
| 2,940,998 | 6/1960 | Ogawa et al. ..................... 562/402 |
| 3,039,932 | 6/1962 | McLimans et al. ................ 435/241 |
| 3,790,598 | 2/1974 | Damico et al. ................. 562/564 X |
| 3,795,704 | 3/1974 | Diery et al. ..................... 562/565 |
| 3,853,906 | 12/1974 | Rogozhin et al. ............. 562/402 X |
| 4,459,355 | 7/1984 | Cello et al. ...................... 435/172.3 |
| 4,464,395 | 8/1984 | Huang ............................ 562/560 X |

OTHER PUBLICATIONS

Chemical Abstracts 87:53558r, 1977.
Chemical Abstracts 89:104050v, 1978.
Chemical Abstracts 92:72381x, 1979.
Bioorganic Chemistry 6, Biellmann, Branlant and Wallen, "Stereochemistry of Octopine and of Its Isomers and Their Enzymatic Properties", 1977, pp. 89–93.
The Journal of Biological Chemistry, vol. 119, No. 2, 1937, Moore and Wilson, "Nitrogenous Extractives of Scallop Muscle", pp. 573–584.
MGG by Springer-Verlag, 1978, Petit and Tempe, "Isolation of Agrobacterium Ti-Plasmid Regulatory Mutants", pp. 147–155.
Science, vol. 218, Nov. 26, 1982, Ream and Gordon, "Crown Gall Disease and Prospects for Genetic Manipulation of Plants", pp. 854–859.
Bull. Chem. Soc. of Japan, 1982, Goto, Waki, Mitsuyasu, Kitajima, and Izumiya, "Configuration of Alanine Part in Natural Octopine", pp. 261–265.

Primary Examiner—Natalie Trousof
Assistant Examiner—Vera C. Clarke
Attorney, Agent, or Firm—Oblon, Fisher, Spivak, McClelland & Maier

[57] ABSTRACT

Novel octopine derivatives are disclosed which are useful for the selective growth of the agriculturally useful *A. tumefaciens* bacterium along with a synthetic method for their preparation. Also disclosed is a method of separating octopine derivatives from their diastereoisomers along with a method of selectively growing strains of the bacterium *A. tumefaciens*.

58 Claims, No Drawings

SYNTHESIS AND ISOLATION OF OCTOPINE AND ITS ANALOGUES

BACKGROUND OF THE INVENTION

1. Field of the Invention

The present invention relates to a method for the isolation of octopine and its analogues from diastereoisomers of these compounds.

2. Description of the Prior Art

Considerable activity exists in the area of genetic engineering of microorganisms. However, only recently has there been significant activity involving genetic engineering of higher plants. One method which has been proposed for introducing genetic material into higher plants involves the use of the bacterium *Agrobacterium tumefaciens* to introduce a crown gall tumor in a dicotyledoneous plant. Variant *A. tumefaciens* bacterial strains contain a large Ti (tumor-inciting) plasmid, part of which, a specific segment called the T-DNA (transferred DNA), integrates into the plant nuclear DNA where it is retained and expressed even after the tumors redifferientiate. Accordingly, the Ti plasmid is a possible vector for accomplishing genetic engineering in plants. See, Ream & Gordon, Crown Gall Disease and Prospects for Genetic Manipulation of Plants", Science 218:854–859 (1982).

Crown gall tumor cells produce opines, which are unusual amino acid derivatives not found in normal plant cells. The ability of transformed cells to synthesize these amino acid derivatives depends strictly on the bacterial strain which causes the tumor. Furthermore, bacteria which induce a specific amino acid derivative can utilize that derivative as a single source of carbon and nitrogen, but cannot utilize opines produced by tumors caused by other strains of bacteria. Accordingly, opines can be utilized in the preparation of bacterial growth media useful for the selection of appropriate strains of bacteria. Other derivatives are toxic to the bacteria containing the appropriate catabolic enzymes coded with the Ti plasmid. See Petit & Tempe, "Isolation of Agrobacterium Ti-Plasmid Regulatory Mutants", Molec. Gen. Genet. 167:147-155 (1978). Use of these derivatives and selected media permits the selection of mutant strains of bacteria which do not have the ability to catabolize the toxic derivatives.

Accordingly, a source of opines useful for producing the selective media is needed. While it is possible to isolate different opines from crown gall tumors of plants, the isolation techniques are tedious and a general synthetic method capable of synthesizing different opines in good yield is needed. See, Firmin & Fenwick, Phytochemistry 16:761-762 (1977).

Synthetic procedures for the synthesis of opines and particularly for the synthesis of D-octopine and its derivatives exist in the prior art but suffer from disadvantages caused by the difficulty of separating D-octopine (or an analogue of D-octopine) from the diastereoisomer produced by the synthetic method, known as L-allooctopine (or the corresponding L-allooctopine analogue).

The aforementioned Petit and Tempe, disclose a chemical synthesis of octopine and analogues based on the general method of Izumiya et al, J. Amer. Chem. Soc. 79:652-658 (1957) involving condensation of an amino acid with the suitable bromo derivative of propionic acid in the presence of barium hydroxide.

Goto et al, Bull. Chem. Soc. Jpn. 55:261-265 (1982), prepare different octopine isomers by reacting the corresponding alanine derivative and 2-Br-5-acetamidopentanoic acid followed by deacetylation and guanidination with an overall yield of 61%. In both these references, precipitation of the octopine isomers was accomplished from a water-ethanol mixture.

Biellman et al, Bioorganic Chemistry 6:89–93 (1977), synthesize the present compounds by reductive deamination with cyanoborohydride with a yield of between 28 and 38%. The compounds were further purified by chromatography on a cationic exchange substrate and the diastereoisomers were separated by fractional crystallization from a water-ethanol mixture.

Moore and Wilson, J. Bio. Chem. 119:573-83 (1937) obtain octopine by aqueous extraction from scallop muscle. After separation from glycogen and protein and a series of various other treatments the resulting solution was concentrated at 40°–50° C. and octopine was allowed to crystallize for several days at 0°–4° C. The product was dissolved in hot water and re-crystallized from an alcohol-water mixture (80%).

Goto et al, also disclose the chemical synthesis of D-octopinic acid as an intermediate in the synthesis of the octopine isomers (see above). The octopinic acid isomers were obtained from alanine and 2-Br-5-acetamidopentanoic acid in the presence of barium hydroxide with a yield of 16%.

Accordingly, an improved method for the separation of octopine and its analogues from their diastereoisomers is necessary in order for these synthetic methods to be fully developed.

SUMMARY OF THE INVENTION

Accordingly, it is an object of the present invention to provide a method of separating octopine or a derivative of octopine from its diastereoisomer whereby octopine or the derivative of octopine are obtained in pure form.

Another object of the present invention is to provide a general method of synthesizing octopine or a derivative of octopine, comprising separating the resulting compounds from their diastereoisomers thereby providing octopine or the derivative of octopine in substantially purified form.

A further object of the present invention is to provide a method of synthesizing octopinic acid or an octopinic acid derivative from octopine or the corresponding octopine derivative.

Still another object of the present invention is to provide growth media comprising the purified octopine derivatives.

Another object is to provide a method of selectively growing strains of the bacterium *A. tumefaciens*. Still another object is to provide a method of selectively growing crown gall tumor cells.

And still a further object is to provide a method of selectively growing bacteria or cells carrying the Ti plasmid or sequences derived from the plasmid.

These and other objects of the invention, as will hereinafter become more readily apparent, have been accomplished by providing a method of separating a compound of the formula:

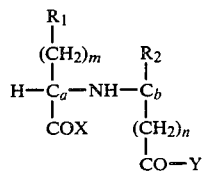

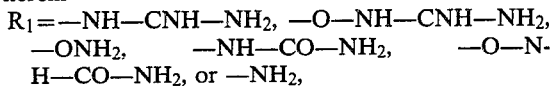

wherein $R_1 =$ —NH—CNH—NH$_2$, —O—NH—CNH—NH$_2$, —ONH$_2$, —NH—CO—NH$_2$, —O—NH—CO—NH$_2$, or —NH$_2$, $R_2 =$ —H, branched or unbranched alkyl of $C_1$-$C_{10}$ or their halo derivatives, X and Y may be the same or different and represent —OH or —NH$_2$, with the proviso that at least one of them is —OH, $C_a$ and $C_b$ may be the same or different and represent the R and S tetrahedral carbon configuration, n=0-1, and m=1-4, from its diastereoisomer, by selective crystallization from an aqueous solution having the approximate isoelectric point of the compound. The diastereoisomer can be crystallized from the mother liquor by adding an organic solvent having a dielectric constant lower than that of water.

A general method of synthesizing octopine or a derivative of octopine is also part of the present invention. This process comprises:

(a) reacting a compound of the formula:

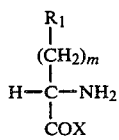

with a compound of the formula:

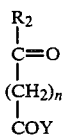

in the presence of sodium cyanoborohydride, (b) separating from the reacting compounds and then drying, the mixture of diastereoisomers obtained in step (a), (c) dissolving the mixture of diastereoisomers in water, and (d) separating octopine or an octopine derivative from its diastereoisomer by using the method hereinbefore described.

The objects of this invention have also been attained by providing a method of synthesizing octopinic acid or a derivative of octopinic acid, comprising:

(a) heating octopine or an octopine derivative wherein $R_1$ is —NH—CNH—NH$_2$ (or its diastereoisomer) in the presence of an alkaline metal hydroxide until the generation of ammonia from the aqueous solution is completed and a crude solution of the octopinic acid derivative (or its diastereoisomer) is formed, (b) separating said derivative from the crude solution therby obtaining a partially purified solid derivative, (c) dissolving the partially purified solid derivative in water thereby obtaining an aqueous solution of the partially purified solid derivative, (d) separating octopinic acid or the octopinic acid derivative from the aqueous solution by using the organic solvent method hereinbefore described.

Other objects of this invention have been attained by providing novel octopine derivatives.

Still another object has been attained by providing growth media for bacteria and cells comprising the purified compounds of this invention.

Further, the objects of the invention have also been obtained by providing a method of selectively growing strains of the bacterium A. tumefaciens, by using media comprising the purified octopine derivatives of this invention.

The objects have also been attained by providing a method of selectively growing cells carrying the Ti-plasmid or sequences derived from the plasmid, by using media comprising the purified octopine derivaties of the present invention.

A method of selectively growing crown gall tumor cells by using media comprising the purified octopine derivatives of this invention is hereby also provided.

Other objects, advantages and features of the present invention will become apparent to those skilled in the art from the following discussion.

DESCRIPTION OF THE PREFERRED EMBODIMENTS

The present invention provides an improved method of separating octopine or a derivative of octopine from its diastereoisomer which provides octopine and/or the derivative in substantially purified form. In addition, this invention also provides an improved method for the purification of the diastereoisomer. The given processes provide an improvement over the previously described methods for the crystallization of octopine and its diastereoisomer. Prior methods resulted in a product wherein octopine was contaminated with L-alloocto-pine (Izumiya et al, Petit and Temple, Goto et al, Moore and Wilson and Biellman et al).

The method of separating octopine or an octopine derivative from its diastereoisomer comprises separating a compound of the formula:

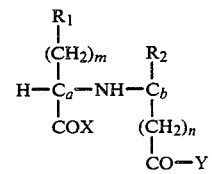

wherein n=0-1, m=1-4, $R_1 =$ —NH—CNH—NH$_2$, —O—NH—CNH—NH$_2$—ONH$_2$—NH—CO—NH$_2$, —O—NH—CO—NH$_2$, or —NH$_2$, $R_2 =$ H, branched or unbranched alkyl of $C_1 \propto C_{10}$ or their halo derivatives, X and Y may be the same or different and represent —OH or —RH$_2$, with the proviso that one of them is —OH, from its diastereoisomer, which comprises:

adjusting the pH of a first aqueous solution containing said compound and its diastereoisomer to the approximate isoelectric point of the compound, whereby a pH-adjusted first solution is obtained;

seeding the pH-adjusted first solution with crystals of the purified first percipitate compound thereby obtaining a seeded first solution;

allowing said seeded solution to stand until a partially purified first precipitate forms and a mother liquor remains; and collecting said precipitate.

Preferred conditions for this method are those where the first aqueous solution contains from 0.001 to 1 g per ml of said compound and its diastereoisomer, the pH of the first solution is adjusted to between about 1-9 and the pH-adjusted solution is allowed to stand at between about 0° to 40° C. until a precipitate develops. Also preferred are conditions were the compound are dissolved in water at between 0.01 to 0.5 g per ml, the pH of the first aqueous solution is adjusted to between 3-7.5, and the pH-adjusted solution is allowed to stand at between about 0° to 20° C. The most preferred conditions are those where the compounds are dissolved at about 0.05 to 0.2 g per ml, the pH of the first aqueous solution is adjusted to about 4.5 to 6 and the pH-adjusted solution is allowed to stand at about 0° to 10° C. The partially purified first precipitate may be collected by filtration. The partially purified precipitate of allooctopine or an allooctopine derivative is obtained with a purity of approximately 99% as determined by chromatography or HPLC.

This method may further comprise the following steps:

resuspending said first partially purified precipitate in water, thereby obtaining a suspension;

heating said suspension until the precipitate substantially dissolves, whereby a second aqueous solution is obtained;

adjusting the pH of said second solution to the approximate isoelectric point of the compound, whereby a pH-adjusted second solution is obtained;

seeding the pH-adjusted second solution with crystals of the purified first precipitate compound thereby obtaining a seeded second solution;

allowing said seeded second solution to stand until a purified first precipitate forms; and collecting said precipitate.

Preferred conditions for the additional steps of this method are similar to the ones hereinbefore described. In addition, the preferred conditions for dissolving the compounds in water are those wherein heating is done at a temperature of between 40° C. and 200° C., and the pH of the second solution is adjusted to between about 1-9. Other preferred conditions for dissolving the compounds in water are those wherein the temperature is between about 60° to 130° C., and the pH of the second solution is adjusted to between about 3 to 7.5. The most preferred conditions are those where the temperature is between about 80° to 110° C. and the pH of the suspension is adjusted to between about 4.5 to 6.

The method of separating octopine or a derivative of octopine from its diastereoisomer may further comprise:

adding to the mother liquor a water-miscible organic solvent having a dielectric constant lower than that of water, and seeding with crystals of the purified second precipitate compound until a partially purified second precipitate forms;

collecting said partially purified second precipitate;

suspending the partially purified second precipitate in a minimum amount of water and heating to dissolve the precipitate, whereby a solution of said partially purified second precipitate is obtained;

adding to the solution of the partially purified second precipitate a water miscible organic solvent having a dielectric constant lower than that of water and seeding with crystals of the purified second precipitate compound until a purified second precipitate forms;

collecting said purified second precipitate.

Some of the preferred conditions for this method are similar to those already described hereinbefore. In addition, the recrystallization of the partially purified second precipitate can be accomplished by heating until a solution of this compound is obtained. Heating can be performed at between 40°-200° C., preferably 60°-130° C. and most preferably at between 80°-110° C. Perferred concentrations for dissolving the precipitate are 0.001-1 g per ml, preferably 0.01-0.5, still more preferred 0.05-0.2.

Some of the preferred conditions for the addition of the organic solvent, are those wherein the solvent is methanol, ethanol or acetone, and the volume of solvent used is between 0.1-20, more preferably between 0.5-15 and most preferred between 1-10 times the volume of water, and the solvent mixture is allowed to stand at between about −40° and 40° C., preferably at between −10° and 20° C., and most preferred range is between 0°-10° C. The precipitate may be collected by filtration, preferably in vacuo, or by lyophilization.

Typically, the purified diastereoisomer compounds which are obtained by these methods have a purity of approximately 98-99% for the purified second precipitate as determined by electrophoresis or HPLC.

The present invention also provides a method of synthesizing octopine or a derivative of octopine and its diastereoisomer, which comprises reacting a compound of the formula:

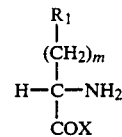

with a compound of the formula:

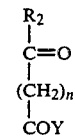

in the presence of cyanoborohydride at a neutral pH thereby obtaining a first solution of a crude mixture of octopine or an octopine derivative in its diastereoisomer;

separating the octopine or the octopine derivative and its diastereoisomer from the reacting compounds, thereby obtaining a diastereoisomer mixture; and separating the octopine or the octopine derivative from its diastereoisomer in the partially purified first mixture by using the methods hereinbefore described.

One of the preferred embodiments of the present invention is that wherein the octopine or octopine derivative is separated from the reacting compounds by:

adjusting the pH of the first solution with the crude mixture of octopine or an octopine derivative and its diastereoisomer to below about 3, thereby allowing the release of HCN and obtaining a pH-adjusted crude solution;

subjecting the pH-adjusted crude solution to cationic chromatography, thereby obtaining a diastereoisomer mixture;

drying the diastereoisomer mixture thereby obtaining a solid diastereoisomer mixture; and dissolving the diastereoisomer mixture in a minimum amount of water by heating, thereby obtaining a solution of octopine or an octopine derivative and its diastereoisomer.

Some of the preferred conditions for the cyanoborohydride reaction are a pH of between 6–8 at temperature between 40°–200° C., more preferable still are a pH of about 7 and a temperature of between about 0°–80° C., and the most preferred is a temperature of between 15°–25° C. Preferred conditions for adjusting the pH of the solution containing the crude diastereoisomer mixture are those wherein the pH is adjusted to below about 2, and most preferably to below about 1. The pH-adjusted crude solution may then be chromatographed on a strong cationic substrate, washed with water, eluted with aqueous ammonia, e.g., 1M ammonia and dried until a powder material is obtained. The chromatographed diastereoisomer mixture may be dried, preferably in vacuo or by lyophilization. The rest of the preferred conditions are as indicated hereinbefore.

The present invention also provides a method for the synthesis of octopinic acid or a derivative of octopinic acid (or allooctopinic acid or a derivative of allooctopinic acid), comprising:

dissolving in aqueous base a compound of the formula:

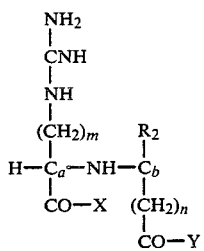

wherein:
$R_1$ is —NH—CNH—NH$_2$

X, Y, $R_2$, n and m are as hereinbefore defined, whereby a basic solution of the compound is formed;

heating said basic solution whereby a product-containing crude solution is obtained;

separating said product from the crude solution, thereby obtaining a partially purified solid product;

dissolving the partially purified solid product in water, thereby obtaining an aqueous solution of the partially purified solid product;

adjusting the pH of the aqueous solution containing the partially purified product to the approximate isoelectric point of the compound, whereby a pH-adjusted solution is obtained;

adding to the pH-adjusted solution a water miscible organic solvent having a dielectric constant lower than that of water, and seeding with crystals of the purified octopinic acid derivative until a partially purified precipitate forms; and collecting said partially purified precipitate.

This method may also comprise the following steps to separate the partially purified solid product from the crude solution:

evaporating the crude solution to dryness whereby a crude solid product is obtained;

dissolving said crude solid product in water to obtain an aqueous solution of the crude product;

adjusting the pH of the solution of the crude product to a pH of below about 3 whereby a pH-adjusted solution of the crude product is obtained;

subjecting the pH-adjusted crude solution to cationic chromatography, thereby obtaining a solution containing a partially purified product; and drying the partially purified product solution to obtain a partially purified solid product.

Some of the preferred conditions for the synthesis of octopinic acid or an octopinic acid derivative are those wherein the starting compound is dissolved at a concentration of between about 0.01–30% (w/v) in a basic solution of approximately 0.01 to 10M base and heating of the basic solution is carried out at between 40°–200° C. for between about 30 min. to 200 hours.

Other preferred conditions are dissolving at about 0.1 to 20% (w/v) in a 0.02–5M base, heating at between about 60°–130° C. for 2–50 hrs. Still most preferred condition are dissolving at about 1–10% (w/v) in a 0.1–2M base and heating at between about 80°–120° C. for about 4–30 hrs. The crude octopinic acid derivative or its diastereoisomer may be liophilized or dried in vacuo.

Preferred conditions for dissolving the crude or partially purified solid octopinic acid derivative or its diastereoisomer are 0.01–30% (w/v), preferably 0.1–20% (w/v). Also preferred conditions for dissolving are 1–10% (w/v), most preferably 3–8% (w/v).

Preferred conditions for adjusting the pH of the solutions of the crude and partially purified octopinic acid derivative are below about 2 and about 1–9, preferably below 1 and about 3–7.5, respectively. The most preferred conditions are those wherein the pH is adjusted to below 1, and 4.5–6, respectively. Cationic chromatography of the pH-adjusted crude solution of the octopinic acid derivative or its diastereoisomer can be done with a strong cationic substrate, e.g., Dowex-50 (H+form)

Drying of the partially purified octopinic acid derivative or its diastereoisomer is preferably done by lyophilization or simply by drying in vacuo.

Octopinic acid derivatives are obtained by the present method with a purity greater than 99%, and a yield of over 67%.

Octopine or an octopine derivative and its diastereoisomers are each obtained by the method of the present invention in a yield greater than 80%. These compounds are obtained with a high degree of purity (90-95% after the first purification step and greater than 98-99% after recrystallization), with simple equipment of widespread use in laboratories. This is, in addition, a very general method for the synthetic preparation of a wide range of compounds of this family. The crystals appear in the solution, e.g. within 24 to 48 hours for D-octopine.

Compounds which can be prepared by the methods of the present invention include those having the following formula:

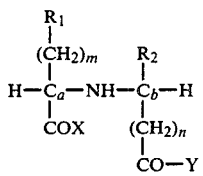

wherein
n=0-1, m=1-4, $R_1 =$ —NH—CNH—NH$_2$, —O—NH—CNH—NH$_2$, —ONH$_2$, —NH—CO—NH$_2$, —O—NH—CO—NH$_2$, or —NH$_2$, $R_2 =$ —H alkyl of C$_1$–C$_{10}$ carbon atoms or their halogenated derivatives, and $C_a$ and $C_b$ may be the same or different and represent the R and S tetrahedric carbon configurations; and X and Y represent —OH, —NH$_2$, with the proviso that at least one of them is —OH.

Some of these compounds were known in the prior art. However, these compounds have never previously been obtained with the degree of purity of the present invention. The structures of the known compounds are shown in FIG. 1. Some of these compounds are D-octopine itself, L-allooctopine, homooctopine, noroctopine, canavanooctopine, D-octopinic acid and ureidooctopine.

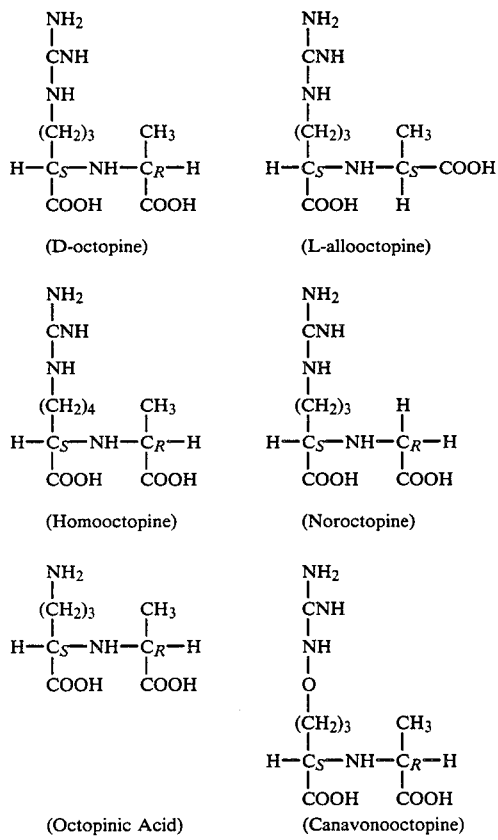

FIG. 1: Known Octopine Derivatives

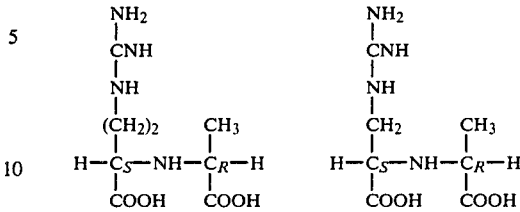

-continued
FIG. 1: Known Octopine Derivatives

All the remaining compounds of this invention are novel and have never been described or suggested prior to this invention.

Some of the preferred compounds having the hereinbefore-described structure, are those wherein $R_1 =$ —NH—CNH—NH$_2$. Another group of preferred compounds are those wherein $R_1 =$ —O—NH—CHN—NH$_2$. Yet another group of preferred compounds are those wherein $R_1 =$ —ONH$_2$. A further preferred group of compounds are those wherein $R_1 =$ —NH—CO—NH$_2$. A further preferred group of compounds are those wherein $R_1 =$ —NH$_2$. Also preferred are the amide derivatives of these compounds, wherein X or Y are —NH$_2$.

Another group of preferred compounds are those wherein $R_2$ is —H or —CH$_3$. Still another group of preferred compounds are those wherein $R_2$ is —CH$_2$CH$_3$. A further group of preferred compounds are those wherein $R_2$ is —CH$_2$F, —CF$_3$ or —CH$_2$Br. Also preferred are amide derivatives of these compounds wherein X or Y are —NH$_2$.

Also preferred are those compounds where $C_a$ and $C_b$ are both in the S carbon configuration. A further preferred group of compounds are those wherein $C_a$ is in the S carbon configuration and $C_b$ is in the R carbon configuration. Another preferred group of compounds are those wherein $C_a$ and $C_b$ are both in the R carbon configuration. Still another preferred group of compounds are those where $C_a$ is in the R carbon configuration and $C_b$ is in the S carbon configuration. Also preferred are amide derivatives of these compounds wherein X or Y are —NH$_2$.

A further preferred group of compounds are those wherein n=0. Still another group of preferred compounds are those wherein n=1. Also preferred are the amide derivatives of these compounds wherein X or Y are —NH$_2$. A further group of preferred compounds are those wherein m=1 or 2. Another group of preferred compounds are those wherein m=3–4. Also preferred are the amide derivatives of these compounds wherein X or Y are —NH$_2$. Also preferred are those compounds wherein $R_1$ is —O—NH—CO—NH$_2$ The compounds of the present invention are useful as a C or N source for the bacterium *A. tumefaciens*. The present invention also provides bacterial growth media, comprising the present compounds. The media may contain, in addition to the present compounds, other nutrients, such as minerals, trace elements, etc. as needed and known in the art of growing bacteria.

A standard method of growing the bacterium is by preparing media comprising a compound of the present invention or a mixture thereof supplemented as needed to support the growth of the bacterium.

This method is useful in selecting the strains of bacterium which can metabolize a specific compound of the present invention. This strain of bacterium will be capable of growing in the presence of a compound of this invention, while other strains which are not capable of metabolizing the compound will perish.

Since the capability for metabolizing the present compound is conferred to the bacterium by the $T_i$ plasmid, genetically engineered *A. tumefaciens* bacteria having specific $T_i$ plasmid vectors or sequences conferring the capability for metabolizing different compounds, can also be selectively grown by using the media comprising the present compounds.

In addition, cells which contain the Ti-plasmid, vectors or sequences derived from the plasmid can also be grown in the media of this invention. Cells which are representative are crown gall tumor cells.

The concentration of the present compounds in the growth media can vary over a wide range as is known by those skilled in the art of growing bacteria or plant cells. Generally, a concentration of between about 0.5 and 20 g per 1, most preferably a concentration of between about 2 and 5 g per 1 for most *A. tumefaciens* bacterial strains or plant cells would be sufficient.

Having now generally described this invention, the same will be understood by reference to certain specific examples which are included herein for purposes of illustration only and are not intended to be limiting unless otherwise specified.

EXAMPLES

EXAMPLE 1

Selective crystallization of D-octopine and L-alloctopine

A mixture of D-octopine and L-alloctopine (41 g) was dissolved in 410 ml of water with gentle heating at 80° C., and the solution was then allowed to cool down to room temperature. The pH was adjusted to about 5.3–5.5 with 2M HCl, and the solution was placed at 0°–5° C. for 24 to 48 hr. after seeding with crystals of L-alloctopine. A white solid (16 g) was filtered and identified as L-alloocotpine (purity 99%). To the filtrate, 9 volumes of methanol were added at room temperature, and the solution was left at 22° C. after seeding with crystals of D-octopine. After 24 to 48 hrs., a white solid was filtered and identified as D-octopine (purity 90–95%). Yield 14–16 g.

Recrystallization of D-octopine was accomplished by dissolving 10 g of D-octopine in 100 ml of water and warming to 80°–90° C. to dissolve. Methanol (9 volumes per volume of water) was added to the solution at room temperature, and the crystals were allowed to form at 22° C. after seeding with crystals of D-octopine. 8 g of D-octopine were obtained (yield 80%) with a purity of 98–99%.

EXAMPLE 2

Synthesis of D-octopine and L-alloctopine 110 g of arginine. HCl and 184 g of pyruvate were reacted in 4.5 l of water at a pH of 7–8.5 with 50 g sodium cyanoborohydride for 24 hr. at room temperature. After the reaction mixture was acidified to a pH of 0.6 and the cyanoborohydride fumes allowed to evolve, the remaining solution was applied to a column containing 1 g of Dowex-50 (H+-form). The column was washed with 1-2 volumns of water and developed with 1M aqueous ammonia. The column effluent which contains the mixture of the compounds was then taken to dryness on a rotary evaporator and D-octopine and L-allooctopine were selectively crystallized as shown in Example 1.

EXAMPLE 3

Synthesis of D-Octopinic Acid 20 g of D-octopine in 100 ml of 1M NaOH was heated at 100° C. for 12–20 hr. The solution was evaporated to dryness to remove the ammonia and then dissolved in water. The pH was adjusted to 0.89 with 6M HCl and the solution was applied to a column of 200 g of Dowex-50 (H+-form). The column was washed with water and then developed with 10% (v/v) aqueous ammonium hydroxide. The fractions that contained ninhydrin-positive material after removal of ammonia were combined, evaporated to dryness on a rotary evaporator, and then dissolved in 100 ml of water. The pH was adjusted to 5.2 with 3M HCl. After the addition of 5 volumes of ethanol, the solution was left at 0°–5° C. for 24 to 48 hr. A white solid was collected by filtration in an amount of 11.1 g, and identified as octopinic acid (67% yield, 99% pure). The absence of significant racemization at the chiral carbon atoms is supported by the fact that the product gave a single peak by HPLC in the 80% methanol in water, partisil SAX column solvent system that separates D-octopinic acid from L-allooctopinic acid and by its optical rotation $((\alpha)_D^{22}=20°$, C 0.5, $H_2O$; publ. 19°).

Having now fully described this invention, it will be appreciated by those of skill in the art that the same can be practiced within a wide and equivalent range of compositions, mode of use, and the like without effecting the spirit or scope of the invention, or any embodiment thereof.

What is claimed as new and intended to be covered by Letters Patent of the United States is:

1. A method of separating a compound of the formula:

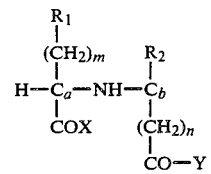

wherein
m=1–4, n=0–1,
$R_1=$ —NH—CNH—$NH_2$, —O—NH—CNH—$NH_2$, —$ONH_2$, —NH—CO—$NH_2$, —O—NH—CO—$NH_2$, or —$NH_2$,
$R_2=$ —H, alkyl of $C_1$–$C_{10}$ carbons or their halogenated derivatives,
X and Y may be the same or different and represent —OH and —$NH_2$, with the proviso that at least one is —OH, from its diastereoisomer, which comprises:
(a) adjusting the pH of an aqueous first solution containing said compound and its diastereoisomer to the appropriate isoelectric point of the compound, whereby a pH-adjusted first solution is obtained;
(b) seeding with purified crystals of the first precipitate compound thereby obtaining a seeded solution;
(c) allowing said seeded solution to stand until a partially purified first precipitate forms and a mother liquor remains; and
(d) collecting said partially purified first precipitate.

2. The method of claim 1, further comprising before step (a), the following step:
   dissolving the compound and its diastereoisomer in water whereby an first aqueous solution is obtained.
3. The method of claim 1, further comprising the following steps:
   (e) suspending said partially purified first precipitate in water whereby a suspension is obtained;
   (f) heating the suspension until the precipitate substantially dissolves thereby obtaining a second aqueous solution;
   (g) adjusting the pH of the second aqueous solution containing the partially purified first precipitate, to the approximate isoelectric point of the compound, whereby a pH-adjusted second solution is obtained;
   (h) seeding said pH-adjusted second solution with crystals of the purified first precipitate compound, thereby obtaining a seeded second solution;
   (i) allowing the seeded second solution to stand until a purified first precipitate forms; and
   (j) collecting the purified first precipitate.
4. The method of claim 1, further comprising the following steps:
   (e) adding to the mother liquor a water-miscible organic solvent having a dielectric constant lower than that of water, and seeding the same with crystals of the purified second precipitate compound thereby obtaining a seeded second precipitate solution;
   (f) allowing the seeded second precipitate solution to stand until a partially purified second precipitate forms; and
   (g) collecting the partially purified second precipitate.
5. The method of claim 4, further comprising:
   (h) suspending the partially purified second precipitate in a minimum amount of water whereby a suspension of the partially purified second precipitate is obtained;
   (i) heating the suspension of the partially purified second precipitate until a solution of said partially purified second precipitate is obtained;
   (j) adding to the solution of the partially purified second precipitate a water-miscible organic solvent having a dielectric constant lower than that of water and seeding the same with crystals of the purified second precipitate compound whereby a seeded solution is obtained; and
   (k) allowing the seeded solution to stand until a purified second precipitate forms; and
   (l) collecting said second precipitate.
6. The method of claim 1 wherein the pH of the first solution is adjusted to between about 1 and 9.
7. The method of claim 1 wherein the seeded solution is allowed to stand at between about 0° C. and 40° C.
8. The method of claim 1 wherein the partially purified first precipitate is collected by filtration.
9. The method of claim 1 wherein the pH is adjusted by using hydrochloric acid.
10. The method of claim 2, wherein the compound is dissolved at a concentration of between about 0.001 to 1.0 g per ml and by heating at between 40° to 200° C.
11. The method of claim 3 wherein the partially purified first precipitate is dissolved at a temperature of between about 40° to 200° C.

12. The method of claim 3, wherein the partially purified first precipitate is suspended in water at between about 0.001 to 1 g per ml.
13. The method of claim 3 wherein the pH of the solution is adjusted to about 1 to 9.
14. The method of claim 1 wherein the pH of the suspension is adjusted with the base selected from the group consisting of NaOH, NH$_4$OH, KOH and LiOH.
15. The method of claim 3 wherein the pH of the second solution is adjusted to about 1 to 9.
16. The method of claim 3 wherein the seeded solution is allowed to stand at about −40° to 40° C.
17. The method of claim 4 wherein the organic solvent is methanol, ethanol or acetone.
18. The method of claim 4 wherein step (f) is carried out at about −40° to 40° C.
19. The method of claim 5 wherein the partially purified second precipiate is dissolved at a concentration of about 0.001 to 1 g per ml.
20. The method of claim 5 wherein the organic solvent is methanol, ethanol or acetone.
21. The method of claim, 5 wherein step (k) is carried out at about −40° to 40° C.
22. A method of synthesizing octopine or an octopine derivative in its diastereoisomer, comprising:
   (a) reacting a compound of the formula:

$$\begin{array}{c} R_1 \\ | \\ (CH_2)_m \\ | \\ H-C-NH_2 \\ | \\ COX \end{array}$$

with a compound of the formula:

$$\begin{array}{c} R_2 \\ | \\ C=O \\ | \\ (CH_2)_n \\ | \\ COY \end{array}$$

wherein
   m=1–4, n=0–1,
   $R_1$=—NH—CHN—NH$_2$, —O—NH—CNH—NH$_2$, —ONH$_2$, —NH—CO—NH$_2$, —O—NH—CO—NH$_2$, or —NH$_2$,
   $R_2$=—H, alkyl of $C_1$-$C_{10}$ carbons and their halogenated derivatives,
   X and Y may be the same or different and represent —OH and —NH$_2$, with the proviso that at least one is —OH, in the presence of cyanoborohydride, thereby obtaining a solution containing a crude mixture of octopine or an octopine derivative and its diastereoisomer;
   (b) separating a crude mixture of octopine or the octopine derivative and its diastereoisomer from the reacting compounds, thereby obtaining a diastereoisomer mixture; and
   (c) separating the octopine or octopine derivative from its diastereoisomer by the method of claim 1.
23. The method of claim 22 wherein step (b) comprises:
   (I) adjusting the pH of the crude mixture of the compound and its diastereoisomer to a pH of below about 3, thereby allowing for the release of HCN, and obtaining a pH-adjusted crude solution;

(II) subjecting the pH-adjusted solution to cationic chromatography, thereby obtaining a diastereoisomer mixture;

(III) drying the diastereoisomer mixture whereby a solid diastereoisomer mixture is obtained; and (IV) dissolving the diastereoisomer mixture in a minimum amount of water, thereby obtaining a solution of octopine or an octopine derivative and its diastereoisomer.

24. The method of claim 22 wherein the reaction of step (a) is carried out at a pH of about 6 to 8.

25. The method of claim 22 wherein the reaction of step (a) is carried out at about $-40°$ to $200°$ C.

26. The method of claim 23 wherein the pH-adjusted crude solution is chromatographed in a strong cationic substrate.

27. The method of claim 23 wherein the diastereoisomer mixture is dissolved at about 0.001–1 g/ml.

28. A method of synthesizing an octopinic acid derivative or its diastereoisomer, comprising:
(a) dissolving in aqueous base a compound of the formula:

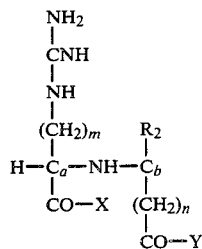

wherein
$m = 1-4$, $n = 0-1$,
$R_2 = $ —H, alkyl of $C_1$-$C_{10}$ carbons and their halogenated derivatives,
X and Y may be the same or different and represent —OH and —NH$_2$, with the proviso that at least one is —OH, whereby a basic solution of the compound is formed;

(b) heating said basic solution whereby a crude solution of the octopinic acid derivative or its diastereoisomer is formed;

(c) evaporating the heated solution to dryness whereby a crude solid product is obtained;

(d) dissolving the crude solid product in a minimum amount of water thereby obtaining a crude product solution;

(e) adjusting the pH of the crude product solution to a pH of below about 3, whereby a pH-adjusted solution is obtained;

(f) subjecting the pH-adjusted solution to cationic chromatography thereby obtaining a partially purified solution of the octopinic acid derivative or its diastereoisomer; and (g) drying the partially purified solution to obtain a partially purified solid octopinic acid derivative or its diastereoisomer.

29. The method of claim 28, further comprising:
(h) suspending the partially purified solid octopinic acid derivative or its diastereoisomer in a minimum amount of water, and heating to dissolve the derivative thereby obtaining a partially purified solution of the octopinic acid derivatives;

(i) adjusting the pH of the partially purified solution to the approximate isoelectric point of the octopinic acid derivative or its diastereoisomer, whereby a pH-adjusted partially purified solution is obtained;

(j) adding to the mother liquor a water-miscible organic solvent having a dielectric constant lower than that of water, and seeding the same with crystals of the purified second precipitate compound thereby obtaining a seeded second precipitate solution;

(k) allowing the seeded second precipitate solution to stand until a partially purified second precipitate forms; and (i) collecting the partially purified second precipitate.

30. The method of claim 28 wherein the compound is dissolved at a concentration of about 0.01 to 30% (w/v).

31. The method of claim 28 wherein the compound is dissolved in 0.001 to 10M base.

32. The method of claim 28 wherein the basic solution is heated to about $40°$ to $200°$ C.

33. The method of claim 28 wherein step (b) is carried out for about 30 min to 100 hrs.

34. The method of claim 28 wherein the crude solid product is dissolved at about 0.01 to 30% (w/v).

35. The method of claim 29 wherein the partially purified octopinic acid derivative or its diastereoisomer are dissolved in about 0.01–30% (w/v).

36. The method of claim 29 wherein the pH of the partially purified solution is adjusted to about 1–9.

37. A compound of the formula:

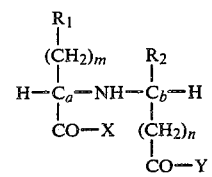

wherein:
$R_1$ is —NH—CNH—NH$_2$, —O—NH—CNH—NH$_2$, —ONH$_2$, —NH—CO—NH$_2$, —O—NH—CO—NH$_2$ or —NH$_2$,
$R_2$ is —H, alkyl of $C_1$-$C_{10}$ carbons or their halo- derivatives,
$C_a$ and $C_b$ may be the same or different and represent the S and R carbon tetrahedral forms,
X and Y are different and represent —OH, or —NH$_2$,
$n = 0-1$, and
$m = 1-4$.

38. The compound of claim 37 substantially free of its diastereoismer.

39. The compound of claim 37, wherein:
$m = 2$;
$R_1$ is —O—NH—CNH—NH$_2$, or —NH$_2$; and
$R_2$ is H or —CH$_3$.

40. The compound of claim 39, substantially free of its diastereoisomer.

41. The compound of claim 37, wherein:
$m = 4$;
$R_1$ is —O—NH—CNH—NH$_2$, or —NH$_2$; and
$R_2$ is H or —CH$_3$.

42. The compound of claim 41, substantially free of its diastereoisomer.

43. The compound of claim 37, wherein:
$R_2$ is H,
$R_1$ is —NH—CNH—NH$_2$, and
$m = 1$.

44. The compound of claim 43, substantially free of its diastereoisomer.

45. The compound of claim 37, wherein
m=2;
$R_1$ is —NH—CNH—NH$_2$; and
$R_2$ is H.

46. The compound of claim 45, substantially free of its diastereoisomer.

47. The compound of claim 37, wherein
m=4;
$R_1$ is —NH—CNH—NH$_2$; and
$R_2$ is H.

48. The compound of claim 47, substantially free of its diastereoisomer.

49. The compound of claim 37, wherein $R_2$ is a F, Cl or Br haloalkyl.

50. A bacterial growth medium, comprising:
   (a) the compound of claim 37 in an amount sufficient to sustain bacterial growth; and
   (b) other supplementary nutrients.

51. A plant cell growth medium comprising:
   (a) the compound of claim 37 in an amount sufficient to sustain plant growth; and
   (b) other supplementary nutrients.

52. A bacterial growth medium comprising:
   (a) the compound of claim 38 in an amount sufficient to sustain plant growth; and
   (b) other supplementary nutrients.

53. A plant cell growth medium, comprising:
   (a) the compound of claim 38 in an amount sufficient to sustain bacterial growth; and
   (b) other supplementary nutrients.

54. A method of selectively culturing an *Agrobacterium tumefaciens* bacterium capable of metabolizing the compound of claim 37, comprising growing the bacterium in the presence of said compound in an amount sufficient to sustain the growth of the bacterium.

55. A method of selectively culturing an *Agrobacterium tumefaciens* bacterium capable of metabolizing the compound of claim 38, comprising growing the bacterium in the presence of said compound in an amount sufficient to sustain the growth of the bacterium.

56. A method of selectively culturing crown gall tumor plant cells capable of metabolizing the compound of claim 37, comprising growing the plant cell in the presence of said compound in an amount sufficient to sustain the growth of the cell.

57. A method of selectively culturing crown gall tumor plant cells containing sequence of the Ti-plasmid and capable of metabolizing the compound of claim 37 comprising growing the cells in the presence of said compound in an amount sufficient to sustain the growth of said cells.

58. A method of selectively culturing crown gall tumor plant cells containing sequences of the Ti-plasmid and capable of metabolizing the compound of claim 38 comprising growing the cells in the presence of said compound in an amount sufficient to sustain the growth of said cells.

* * * * *